(12) United States Patent
Beck et al.

(10) Patent No.: US 9,332,970 B2
(45) Date of Patent: May 10, 2016

(54) FULL CORE BIOPSY DEVICE

(75) Inventors: Deborah R. Beck, Indianapolis, IN (US); Dan C. Ireland, Martinsville, IN (US)

(73) Assignee: Kohala Inc., Indianapolis, IN (US)

( * ) Notice: Subject to any disclaimer, the term of this patent is extended or adjusted under 35 U.S.C. 154(b) by 755 days.

(21) Appl. No.: 13/614,078

(22) Filed: Sep. 13, 2012

(65) Prior Publication Data

US 2013/0053725 A1  Feb. 28, 2013

Related U.S. Application Data

(63) Continuation-in-part of application No. 13/190,808, filed on Jul. 26, 2011, and a continuation-in-part of application No. 12/970,761, filed on Dec. 16, 2010, now Pat. No. 9,237,883.

(60) Provisional application No. 61/564,633, filed on Nov. 29, 2011, provisional application No. 61/368,119, filed on Jul. 27, 2010, provisional application No. 61/308,024, filed on Feb. 25, 2010.

(51) Int. Cl.
| | |
|---|---|
| *A61B 10/02* | (2006.01) |
| *A61B 17/3205* | (2006.01) |
| *A61B 17/32* | (2006.01) |
| *A61B 17/34* | (2006.01) |
| *A61B 10/00* | (2006.01) |
| *A61B 19/00* | (2006.01) |

(52) U.S. Cl.
CPC ......... *A61B 10/0233* (2013.01); *A61B 10/0275* (2013.01); *A61B 10/0283* (2013.01); *A61B 17/32053* (2013.01); *A61B 2010/0093* (2013.01); *A61B 2017/320064* (2013.01); *A61B 2017/3447* (2013.01); *A61B 2019/462* (2013.01)

(58) Field of Classification Search
CPC ........... A61B 10/0233; A61B 10/0266; A61B 10/0275; A61B 10/0283; A61B 2017/3447; A61B 2017/320064; A61B 17/32053
See application file for complete search history.

(56) References Cited

U.S. PATENT DOCUMENTS

| | | | |
|---|---|---|---|
| 4,512,344 A | 4/1985 | Barber | |
| 4,907,598 A | 3/1990 | Bauer | |

(Continued)

FOREIGN PATENT DOCUMENTS

| | | |
|---|---|---|
| RU | 13534 U1 | 4/2000 |
| SU | 1404068 A1 | 6/1988 |

(Continued)

OTHER PUBLICATIONS

International Search Report corresponding to International Application No. PCT/US/2012/067019 date of mailing Feb. 28, 2013 (7 pages).

(Continued)

*Primary Examiner* — Devin Henson
(74) *Attorney, Agent, or Firm* — Maginot, Moore & Beck, LLP

(57) ABSTRACT

A biopsy device includes coaxially disposed inner and outer needles in which the outer needle tip is configured for obtaining a tissue sample. The inner surface of the outer needle includes a tissue retention feature which may include a countersink and/or a feature formed in the inner surface. The device may be introduced to a biopsy site through an introducer in which the introducer is vented and/or a certain ratio of introducer inner diameter and biopsy device outer diameter is maintained.

14 Claims, 13 Drawing Sheets

(56) References Cited

U.S. PATENT DOCUMENTS

| | | |
|---|---|---|
| 5,313,958 A | 5/1994 | Bauer |
| 5,490,521 A | 2/1996 | Davis et al. |
| 5,535,755 A | 7/1996 | Heske |
| 5,655,542 A | 8/1997 | Weilandt |
| 5,788,651 A | 8/1998 | Weilandt |
| 5,916,175 A | 6/1999 | Bauer |
| 6,015,391 A | 1/2000 | Rishton et al. |
| 6,083,237 A | 7/2000 | Huitema et al. |
| 6,126,617 A | 10/2000 | Weilandt et al. |
| 6,196,978 B1 | 3/2001 | Weilandt et al. |
| 6,258,045 B1 | 7/2001 | Ray et al. |
| 6,322,523 B2 | 11/2001 | Weilandt et al. |
| 6,494,844 B1 * | 12/2002 | Van Bladel ............ A61B 18/02 600/567 |
| 6,689,072 B2 | 2/2004 | Kaplan et al. |
| 6,918,881 B2 | 7/2005 | Miller et al. |
| 7,104,945 B2 | 9/2006 | Miller |
| 7,137,956 B2 | 11/2006 | Nishtalas et al. |
| 7,608,049 B2 | 10/2009 | Goldenberg |
| 7,854,706 B2 * | 12/2010 | Hibner ........................ 600/566 |
| 8,157,746 B2 * | 4/2012 | Eberle ................ A61B 10/0233 600/564 |
| 2006/0173377 A1 * | 8/2006 | McCullough ...... A61B 10/0275 600/566 |
| 2007/0106176 A1 | 5/2007 | Mark et al. |
| 2007/0142744 A1 | 6/2007 | Provencher |
| 2008/0071193 A1 * | 3/2008 | Reuber ............. A61B 10/0275 600/567 |
| 2008/0234602 A1 * | 9/2008 | Oostman ............ A61B 10/0266 600/564 |
| 2009/0088666 A1 * | 4/2009 | Miller et al. .................. 600/568 |
| 2009/0143808 A1 | 6/2009 | Houser et al. |
| 2009/0204020 A1 | 8/2009 | Miller et al. |
| 2009/0275858 A1 | 11/2009 | Hardin |
| 2010/0317997 A1 * | 12/2010 | Hibner ............... A61B 10/0275 600/567 |
| 2011/0152715 A1 | 6/2011 | Delap et al. |
| 2011/0208089 A1 | 8/2011 | Sundheimer et al. |
| 2012/0010527 A1 | 1/2012 | Sundheimer et al. |

FOREIGN PATENT DOCUMENTS

| | | |
|---|---|---|
| WO | 2005013831 A2 | 2/2005 |
| WO | 2008115526 A2 | 9/2008 |

OTHER PUBLICATIONS

W F Dahnert, et al., Fine-needle aspiration biopsy of abdominal lesions: diagnostic yield for different needle tip configurations, Radiology, Oct. 1992, abstract, vol. 185—iss.1, Radiological Society of North America, Inc.

BioPince product description, web page screen print dated Nov. 16, 2010, Angiotech Pharmaceuticals, Inc., copyright date 2007-2010.

Partial International Search Report corresponding to PCT/US2012/067019, dated 07.09.15 (6 pages).

* cited by examiner

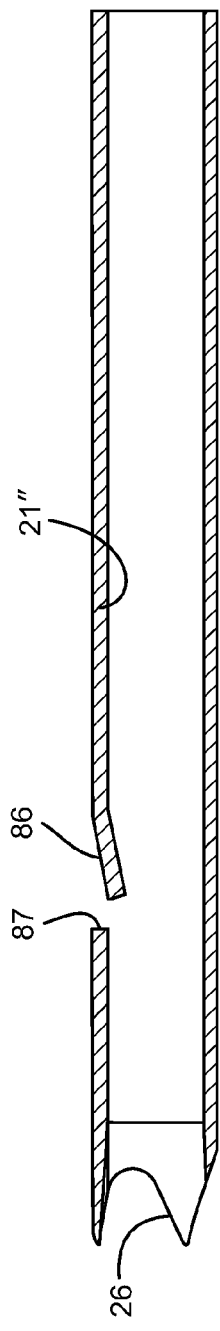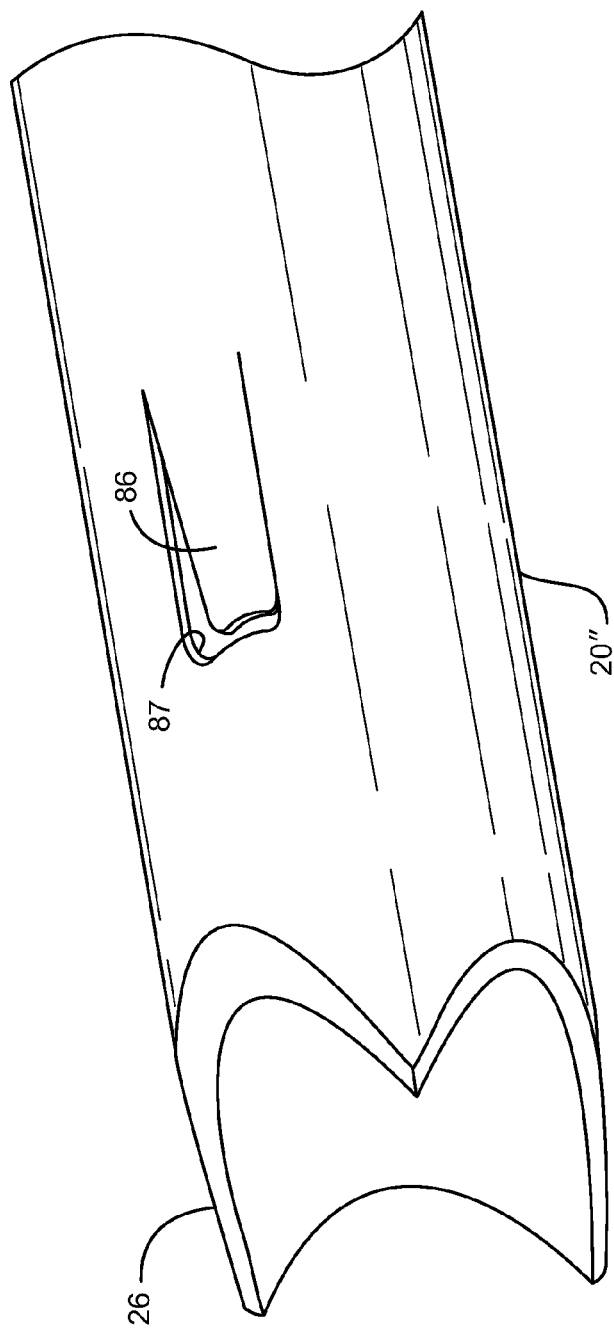

FULL CORE BIOPSY DEVICE

CLAIM OF PRIORITY

This application claims priority to and is a continuation-in-part of co-pending U.S. application Ser. No. 13/190,808, filed on Jul. 26, 2011, entitled "Full Core Biopsy Device", the entire disclosure of which is incorporated herein by reference, which claims priority to U.S. Provisional Application No. 61/368,119 filed on Jul. 27, 2010. This application further claims priority to and is a continuation-in-part of co-pending U.S. application Ser. No. 12/970,761, the entire disclosure of which is incorporated herein by reference, which was filed on Dec. 16, 2010, and which claims priority to the '119 Provisional and to U.S. Provisional Application No. 61/308,024, filed on Feb. 25, 2010. This application further claims priority to and is a non-provisional filing from U.S. Provisional Application No. 61/564,633, filed on Nov. 29, 2011, the entire disclosure of which is incorporated herein by reference.

BACKGROUND

The present invention relates to devices for obtaining a tissue biopsy sample, and more particularly to a device for obtaining a soft tissue core biopsy sample.

Clinicians obtain biopsy specimens for the purpose of diagnosing, staging and grading disease states. One type of biopsy device is a core biopsy needle, which typically operates by coaxial action of an inner needle or stylet having a specimen notch and an outer needle or cannula having a sharp end, with the tip of the inner stylet proud of the end of the outer cannula. The stylet is advanced so that the specimen notch is exposed to tissue, which prolapses into the notch. The cannula is then advanced over the stylet so that the sharp end of the cannula severs the tissue leaving the specimen in trapped within the notch. The volume of the specimen is limited by the notch and the inner diameter of the cannula.

In many biopsy situations, clinicians may desire a full, rounded core sample. The larger cross-section and volume of tissue can provide a more accurate assessment of the tissue pathology. It is also desirable to obtain full, clean core samples that have not been crushed by devices penetrating into tissue, since "crush artifacts" can compromise the analysis of the retrieved sample. In addition, the larger volume of the full core may often provide enough tissue so that only a single pass of the biopsy needle is required. Moreover, it may be desirable to obtain a core sample without having to penetrate past a desired depth of tissue in order to obtain a corresponding desired depth of core sample. It is preferable to insert a biopsy needle only as far as necessary to obtain the desired core sample. It is also desirable to maximize the amount of tissue obtained through the smallest diameter access into the patient.

Coring devices are well known for obtaining samples of hard tissue such as bone. These coring devices include an outer needle having a sharpened edge that is manually pushed and rotated into bone. In this case the rigidity of the tissue—e.g., bone—assures a generally intact full core sample. However, soft tissues do not have the same rigidity and are prone to flow away from the cutting needle. One known device capable of obtaining full core samples of soft tissues is the FNA (fine needle aspiration) device. This device typically includes an outer needle having a sharpened edge at the tip. The outer needle is typically manually moved back and forth while rotating the needle into the target tissue. The use of aspiration helps pull the tissue into the FNA needle. Obtaining core samples in this manner requires a certain amount of dexterity to "tease" the tissue into the needle. Thus, the success of the biopsy is typically technique dependent. Moreover, the FNA procedure takes time ensure that a suitable sample is obtained. In many cases, multiple attempts are required to obtain an adequate sample, which exposes the patient to further discomfort and pain.

Partially and fully automated biopsy devices simplify and shorten the biopsy procedure, but generally eliminate the ability to "tease" the tissue into the coring cannula or needle. While an FNA device may be advanced into soft tissue at a rate of 2 cm/min, a typical automated biopsy device advances the outer needle into the tissue at a rate of 200 cm/min. At these speeds the coring needle has a tendency to push the tissue aside, rather than to draw the tissue into the needle. There is a continuing need for biopsy devices, and particularly full core biopsy devices, which can quickly and efficiently obtain large, intact tissue samples. The need is particularly acute for soft tissue samples because the soft tissue can be difficult to extract and retain without damage to the tissue.

SUMMARY

In one aspect, a biopsy device comprises coaxially disposed inner and outer needles in which the outer needle includes an outer needle having a tissue slicing feature configured for cutting tissue and an inner surface including a tissue retention feature defined therein. In one embodiment, the tissue retention feature may include a countersink formed at the tip. The countersink may be tapered from the tip toward the distal end of the outer needle. In another aspect, biopsy device is introduced to the biopsy site through an introducer cannula. The cannula may be provided with a vent opening to reduce hydrostatic pressure experienced within the introducer when the biopsy device is fired. In another feature, the inner diameter of the introducer cannula and the outer diameter of the outer needle of the biopsy device are maintained at a predetermined ratio to produce optimum performance of the system.

DESCRIPTION OF THE FIGURES

FIG. 9 is a side cross-sectional view of an outer needle component modified to include a retention tab.

FIG. 10 is a perspective view of the end of the outer needle component shown in FIG. 9.

DETAILED DESCRIPTION

Figure 1:
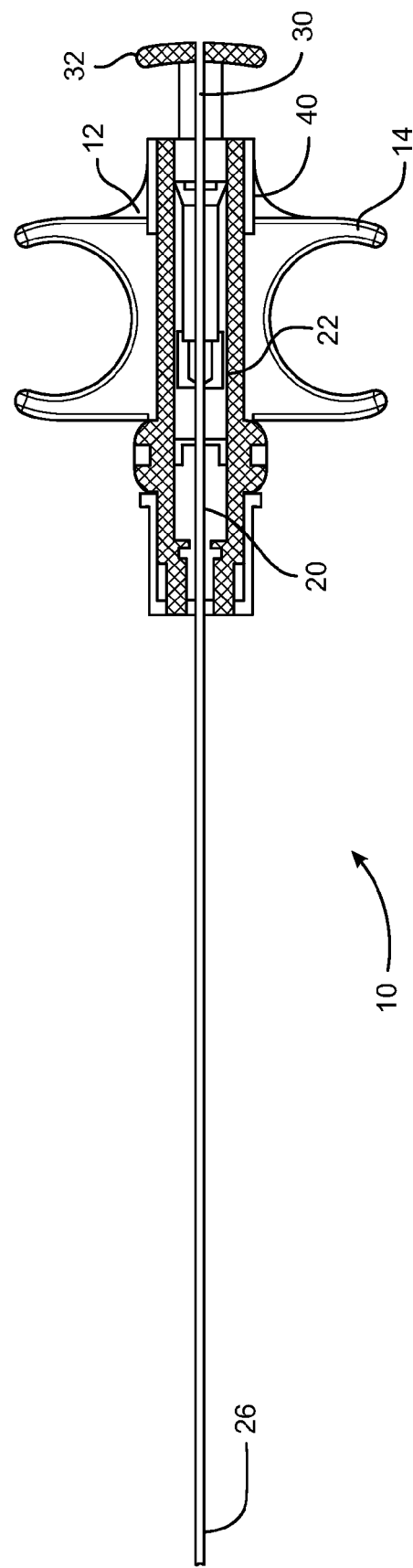
FIG. 1 is a top cross-sectional view of a biopsy device of the prior art.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

One type of core biopsy device 10 is shown in FIG. 1. The device may include features found in the SABD™ core biopsy system sold by US Biopsy of Franklin, Indiana, or similar devices capable of obtaining a core tissue sample from a patient. Although the present disclosure relates to a core biopsy device, the features disclosed herein may be incorporated into other types of tissue sampling or tissue biopsy devices. The device 10 includes a housing 12 that defines finger handles 14 to be grasped by the clinician during a biopsy procedure. The device can include an outer cannula or needle 20 and an inner stylet, cannula or needle 30 coaxially extending through the outer needle 20.

Figure 2:
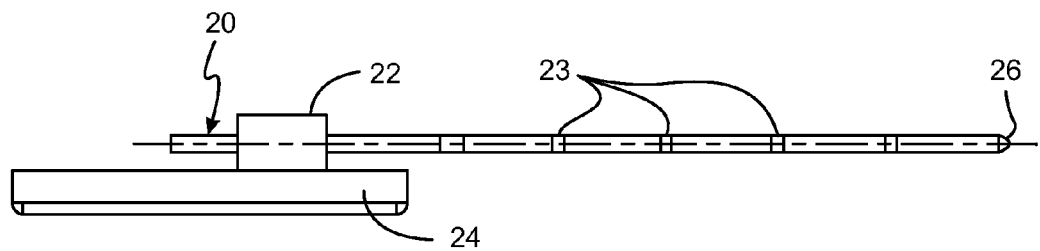
FIG. 2 is a side view of an outer needle component of the biopsy device shown in FIG. 1.
Figure 3:
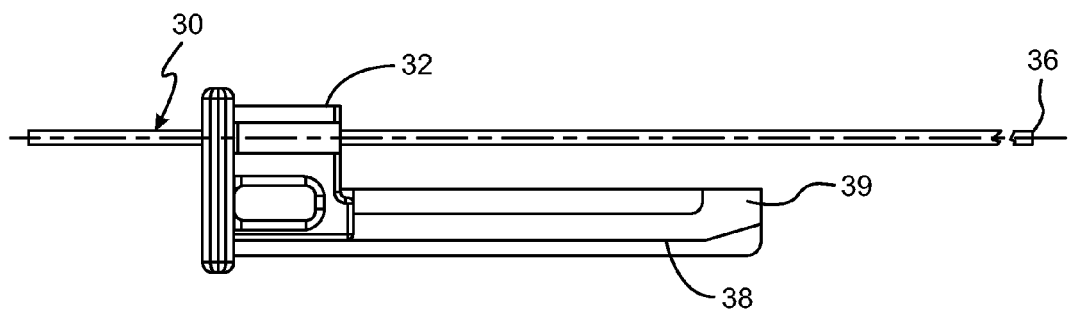
FIG. 3 is a side view of an inner needle component of the biopsy device shown in FIG. 1.

The biopsy device 10 incorporates a mechanism for charging and firing the outer needle relative to the inner needle in order to capture a tissue sample. One embodiment of a firing mechanism is described herein although other mechanisms are contemplated that permit charging and firing the outer needle relative to the inner needle to obtain a tissue sample, including semi or fully automated systems. As shown in more detail in FIG. 2, the outer needle 20 is fixed within an outer needle hub 22 mounted on an outer needle carriage 24. Similarly, as shown in FIG. 3, the inner needle 30 is fixed within an inner needle hub 32 mounted on an inner needle carriage 38. The inner needle carriage 38 includes a tab 39 for engaging the outer needle carriage 24 when the biopsy device 10 is charged. The outer needle 20 may include markings 23 used to determine the depth of the outer needle 20 upon insertion into the patient.

Referring back to FIG. 1, the device 10 includes a spring 40 disposed between the housing 12 and the outer needle hub 22. As is known, the device 10 may include a latch (not shown) that holds the outer needle 20 in its charged position. As with many similar biopsy devices, the device 10 is charged by pulling back on the inner needle hub 32, which in turn pulls the outer needle carriage 24 back until it is engaged by the latch. As the outer needle hub 22 is retracted it compresses the spring 40 within the housing 12.

The biopsy device 10 may be fired by pushing the inner needle hub 32 forward so that the tab 39 trips the latch, although other firing mechanisms may be implemented. Once the latch is released the spring 40 propels the outer needle 20 forward over the inner needle and into the subject tissue. In a biopsy procedure, the clinician positions the tip 26 of the outer needle 20 against the tissue to be sampled, with the device in its charged position. When the device is fired, the outer needle 20 advances directly into the tissue so that a core of tissue is captured within the lumen 21 (FIG. 6) of the outer needle 20. The device 10 can be removed from the patient and the tissue core retrieved from the outer needle 20 in a known manner.

As thus far described, the device 10 may be similar in structure and operation to the SABD™ biopsy system and other similar coaxial single action core biopsy devices. The present invention provides improvements to devices of this type and more particularly improvements to the outer and inner needles for use with such devices. However, it is understood that the features described herein may be incorporated into other types of tissue sampling or biopsy devices, including devices using a motor to charge and/or fire the device.

Figure 4A:
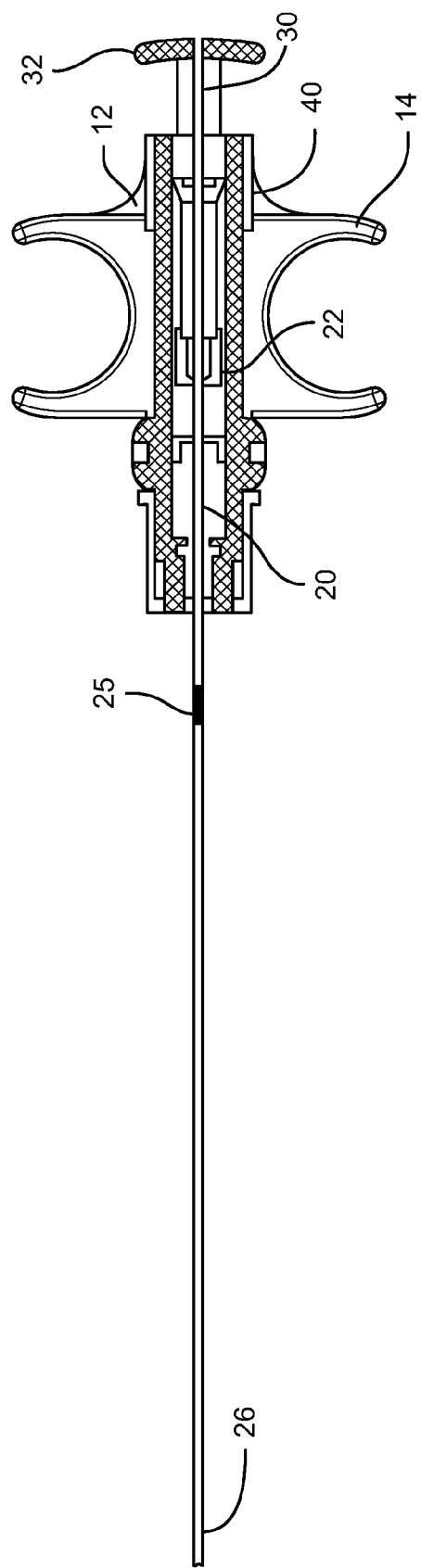
FIGS. 4A-4B are top views of a full core biopsy device incorporating a charging indicator, with the device shown in a neutral and a charged condition.
Figure 4B:
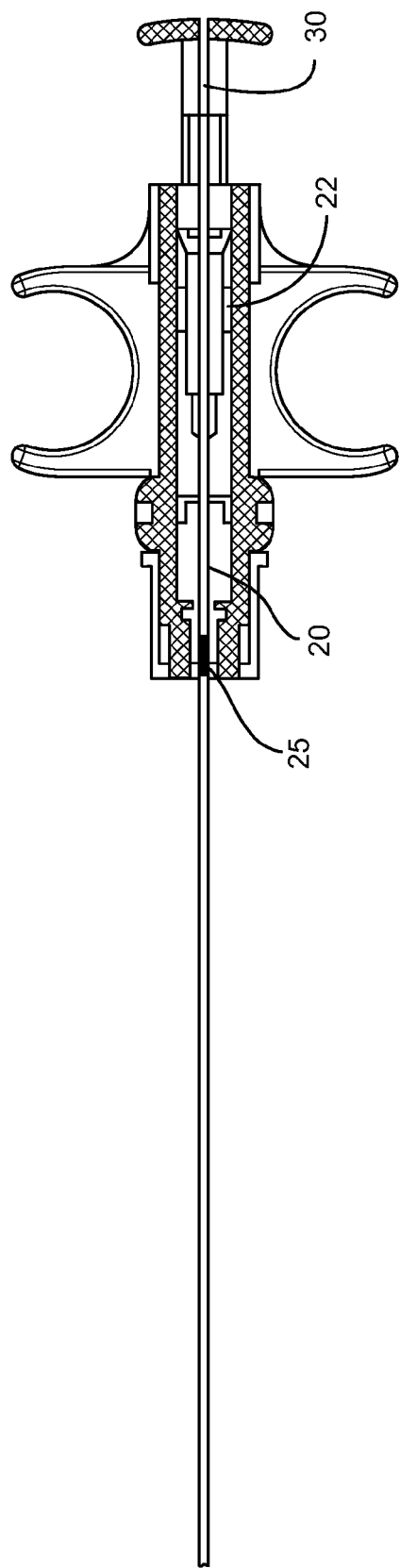

In one improvement, the outer needle 20 is provided with a charging indicator 25, as shown in FIGS. 4a-4b. The charging indicator 25 is a stripe arranged on the outer needle to be visible when the device is in its neutral or un-charged position, as illustrated in FIG. 4a. When the device is charged, the outer needle 20 is withdrawn relative to the housing 12 so that the charging indicator 25 is hidden within the housing, as depicted in FIG. 4a. The indicator thus provides immediate visible evidence that the deice 10 is properly charged and ready to be fired to obtain the biopsy sample. In one embodiment the charging indicator stripe is a 10 mm wide strip formed by etching, although other dimensions and method of manufacture are contemplated.

Figure 5:
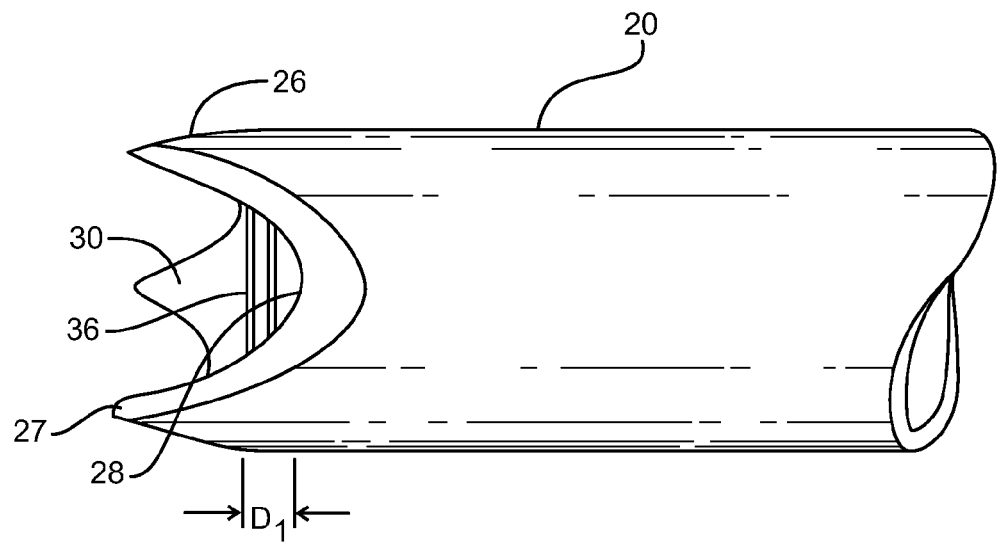
FIG. 5 is an enlarged side view of the end of an outer needle component for use with the full core biopsy device shown in FIG. 1, with the inner needle in its extended position.
Figure 6:
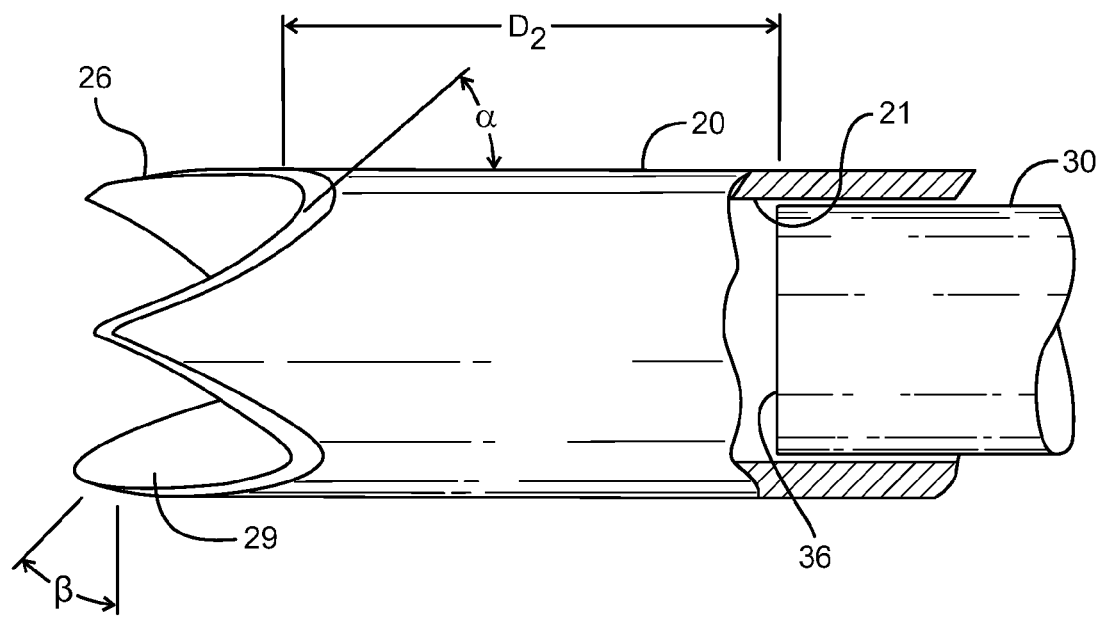
FIG. 6 is an enlarged side view of the end of the outer needle component for use with the full core biopsy device shown in FIG. 1, with the inner needle in its retracted position.

According to one aspect, the outer needle 20 is provided with a Franseen tip 26, as shown in FIGS. 5-6. The Franseen tip includes three or more prongs 27 separated by valleys 28 around the circumference of the outer needle tip 26. In one specific embodiment, three prongs 27 are each defined at an angle α, which may be about 18°. The edge surfaces 29 of the prongs 27 may be defined at an angle β, which may be about 30°, to form a sharp cutting edge within the valleys 28. The prongs 27 permits smooth piercing of the soft tissue as the outer needle 20 initially advances into the tissue and solid purchase once the outer needle has been fully advanced. The prongs 27 are configured to advance through the tissue without substantially compressing the tissue. The angled edge surfaces 29 of the prongs 27 act as guillotine cutters to slice cleanly through the tissue as the outer needle 20 advances.

In accordance with one aspect of the disclosed embodiments, the inner needle 30 is maintained in a retracted position relative to the tip 26 of the outer needle 20 when the device 10 is charged as well as when the device 10 is fired. Thus, as shown in FIG. 5, the tip 36 of the inner needle 30 extends only a dimension D1 from the base of the valleys 28 of the tip 26 when the inner needle hub 32 has been moved to trip the latch and release the outer needle 20 as explained above. When the device 10 is initially charged the inner needle tip 36 preferably does not extend beyond, or extends only minimally beyond, the base of the valleys 28 of the tip 26 of the outer needle 20. Put another way, the tip 36 of the inner needle 30 is always offset rearward from the distalmost ends of the prongs 27 of the tip 26 of the outer needle 20, as depicted in FIG. 5. In one embodiment, the dimension D1 is less than about one-fourth of the length of the prongs 27 (i.e., the distance between the base of the valleys 28 and the distal end or top of the prongs 27).

It can be appreciated that in the charged position shown in FIG. 5, the inner needle hub 32 is in position to fire the device 10. Since the device 10 is fired by moving the inner needle hub 32 forward, as explained above, the tip 36 of the inner needle 30 may contact soft tissue if it resides too proud of the outer needle 20. In prior devices the inner stylet extends beyond the end of the outer cutting cannula prior to firing which tends to push the soft tissue away from the cutting cannula, resulting in less than a full core sample or a sample with a crush artifact. In the embodiments disclosed herein, the arrangement of the inner needle 30 relative to the outer needle 20 in the charged and firing positions avoids this condition found in prior devices. It can be appreciated that this positional relationship is produced by appropriate sizing of the length of the outer needle 20 and inner needle 30 taking into account the configuration of the charging and firing mechanism. The inner needle 30 thus has a length that maintains the inner needle tip 36 in the position shown in FIG. 5 when the inner needle hub 32 has been advanced to release the latch holding the outer needle hub 22 against the compressed firing spring 40.

In yet another approach, the inner needle 30 can be mounted within the inner needle hub 32 to permit deliberate retraction of the inner needle 30 prior to firing to ensure that the inner needle tip 36 is clear of the outer needle tip 26. Thus, a threaded arrangement may be incorporated between the inner needle 30 and the inner needle hub 32 configured so that rotation of the inner needle 30 backs the needle out from the inner needle hub 32. As the inner needle 30 backs out relative to the inner needle hub 32, the inner needle tip 36 is retracted from the outer needle tip 26. The threaded engagement may be configured to prevent complete disengagement of the inner needle 30 from the inner needle hub 32 and may preferably incorporate a locking mechanism to lock the inner needle 30 in its retracted position when the biopsy device 10 is fired. With this embodiment, once the biopsy device 10 is charged the clinician takes the additional step of rotating the inner needle 30 to retract the tip 36 prior to firing the device. The inner needle 30 may be provided with a finger tab at its proximal end to facilitate manual rotation of the needle.

As shown in FIG. 6, after the device 10 is fired, the inner needle 30 is offset rearward from the tip 26 of the outer needle 20 by a dimension D2 because the outer needle 20 has been driven forward by the firing spring 40. This dimension is calibrated to the length of the tissue core desired and is generally based on the throw of the device 10 achieved by the charging and firing mechanism—i.e., the distance that the outer needle 20 travels when propelled by the spring 40. In certain full core biopsy devices the throw of the outer needle may be fixed, while in other such devices the throw may be adjustable to vary the length of the tissue sample that is obtained.

After the device has been fired, the excised tissue sample is retained within the end of the outer needle 20. The inner needle 30 may then be used to expel the tissue sample. This can be accomplished by charging the device—i.e., by pulling back on the inner needle hub 32—which withdraws the outer needle 20 to its initial charged position. With the outer needle 20 charged, the inner needle 30 can be freely advanced forward far enough to push the tissue sample out of the outer needle 20, but not so far as to release the latch and dry fire the device 10. The inner needle 30 would thus be advanced to the position shown in FIG. 5. Since the inner needle 30 is used to expel the sample, it is desirable that the tip 36 of the inner needle 30 be immediately proximate the base of the valleys 28 of the tip 26 of the outer needle 20. This position of the inner needle tip 36 will ensure that the soft tissue sample is dislodged from the outer needle 20 either freely or with only minor urging so as not to destroy the sample.

In certain uses of the device 10 the preferred initial step may be to insert an introducer and stylet to the biopsy site. The stylet is removed and the device 10 is charged and passed through the introducer until the outer needle tip 26 is initially engaged with the soft tissue. The device 10 is then fired and removed through the introducer. To remove the biopsy sample, the device 10 is charged again and the inner needle 30 is slowly advanced forward as the device 10 itself is moved backward over the receiving surface (similar to putting icing on a cake). Once the inner needle 30 reaches the end of its stroke, the biopsy sample should be fully and cleanly dislodged from the outer needle 20.

It can be appreciated that the action of the inner needle 30 is an important factor in producing an intact full-core biopsy sample. The inner needle tip 36 may be closed so that tissue cannot migrate into the inner needle 30. The inner needle tip 36 may be slightly concave to urge the trailing tissue toward the center of the inner needle 30. The inner needle 30 is sized for a close running fit within the inner lumen 21 of the outer needle 20 (FIG. 6), and to prevent passage of tissue into the gap between the inner needle 30 and outer needle 20.

It can be appreciated that the combination of the Franseen tip 26 and the relative positioning between the inner needle 30 and outer needle 20 described above provides a significantly greater chance of obtaining a full, clean core biopsy sample that has not been crushed without having to penetrate past a desired depth of tissue in order to obtain a corresponding desired depth of core sample. The Franseen tip 26 of the device 10 provides a cleaner cut with only linear motion and without rotation of the outer needle 20. This helps reduce the chance of crushing the sample. The relative position of the inner needle 30 and the outer needle 20 also reduces the chance of crushing the sample and helps reduce the depth in the tissue that the device 10 must travel to obtain its full, clean core biopsy sample.

As explained above, hard tissue, such as bone, is readily drawn into a biopsy device and withdrawn by manipulating the device. It is believed that the friction between the tissue core and the inner wall of the biopsy needle holds the core within the needle as it is withdrawn. In the case of hard tissue, the device can be manipulated slightly after the sample has been obtained to ensure that the sample cleanly separates from the native tissue. However, for soft tissue biopsies the ability to retain a long core sample and separate it from the native tissue has been problematic. It is believed that at least part of the difficulty is that there is insufficient friction force between the core sample and the inner wall of the biopsy needle to hold the core in place as the needle is withdrawn. The inherent resilience of the tissue often renders manipulation of the needle ineffective at separating the sample from the native tissue. It has been found that a particular aspect ratio of sample length to sample diameter is needed to obtain a good soft tissue sample. This aspect ratio varies depending upon the type of tissue and its lubricity.

For example, liver tissue is particularly lubricious so that the coefficient of friction between liver tissue and the smooth inner wall of a stainless steel biopsy needle is low. Where the coefficient of friction is low a longer sample is required to achieve the necessary friction force to resist the resistance of the tissue to tearing or separation. In the case of liver tissue, an aspect ratio of 20:1-25:1 has been found suitable for cleanly extracting a liver tissue sample. Thus, in the case of a 16 gauge needle having a nominal inner diameter of 0.0535 in. the tissue sample must be about 1.1-1.3 in. long in order to obtain a viable sample. A smaller 20 gauge needle requires a sample length of about 0.6-0.75 in. to obtain a viable sample. To obtain a sample of these lengths the stroke of the outer needle 20 must exceed the desired sample length. Thus, to obtain a 1.3 in. sample with a 16 gauge needle, the needle stroke is preferably at least 1.4 in. It has been found that for a prior full core biopsy needle construction viable tissue samples can sometimes be obtained but more often than not only after multiple attempts.

Figure 7:
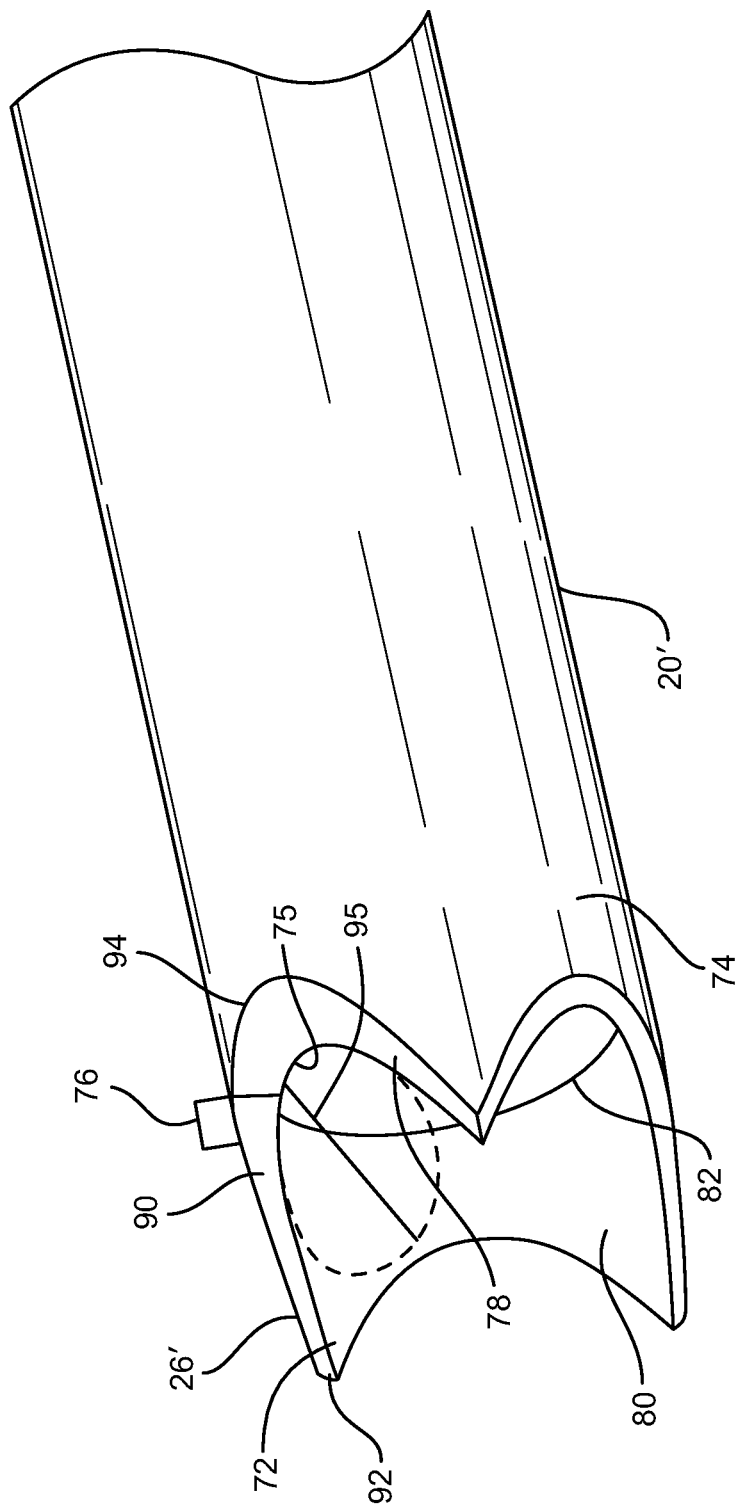
FIG. 7 is an enlarged view of an outer needle according to a further embodiment for use with the full core biopsy core device of FIG. 1.
Figure 8:
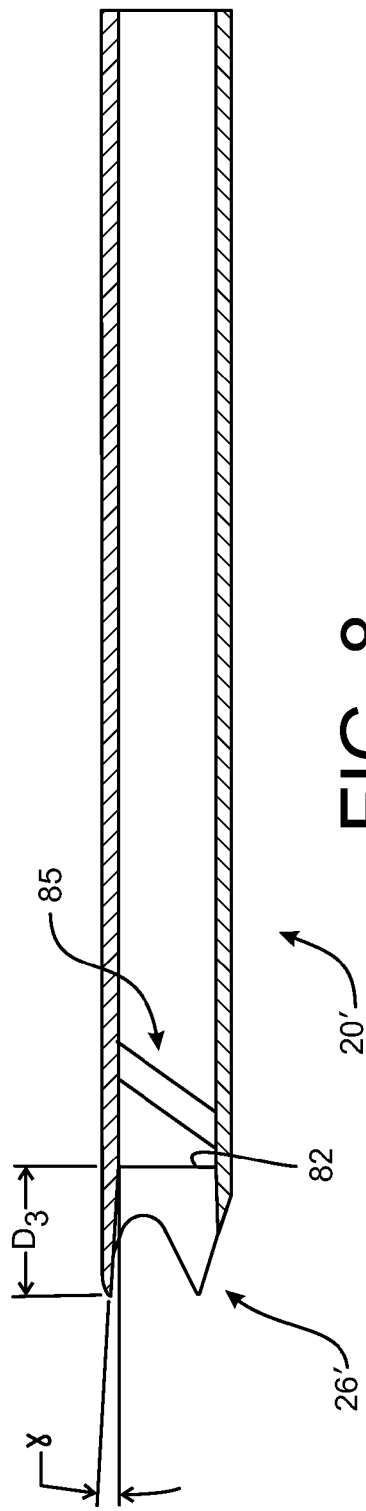
FIG. 8 is a side cross-sectional view of the outer needle component shown in FIG. 7.

In order to address this difficulty, a full core biopsy device according to another embodiment, provides a feature for improving the ability of the outer needle to drawn in and retain a long tissue sample. According to this embodiment, as shown in FIGS. 7-8, an outer needle 20' includes an inner surface 72 and an outer surface 74. The outer needle 20' defines a thickness 76 between the inner surface 72 and the outer surface 74. In one aspect, this retention feature includes a countersink or forcing cone 80 defined in the inner surface 72. The forcing cone 80 essentially "forces" or squeezes more tissue into the outer needle as it is advanced into the tissue. It is believed that the tissue squeezed into the outer needle by the forcing cone leads to an increased friction force between the sample and the needle that holds the sample even when the sample length falls outside the desirable aspect ratio discussed above. Thus, a 16 gauge needle with the forcing cone 80 disclosed herein can obtain an intact tissue sample having a length of less than 1.0 in (vs. the 1.1-1.3 in. length described above). In other words, the forcing cone allows the full core biopsy device disclosed herein to obtain a viable tissue sample with a minimum stroke. Of course, longer samples may be obtained with longer strokes, if desired.

The forcing cone further leads to a sharper cutting edge 78 at the tip of the outer needle. In particular, the cutting edge of an outer needle may be formed by grinding the outer surface 74 of the needle 20', either to a sharp edge or to a Franseen grind as depicted in FIG. 7. The forcing cone 80 may then be formed by grinding the inner surface 72 at an appropriate cone angle γ. The intersection between the outer and inner surface grinds thus creates a sharper cutting edge 78 than either grind alone.

The countersink or forcing cone 80 is formed in the inner surface 72 of the outer needle 20' and extends from the tip to an inner end 82. The inner end 82 is located at a depth D3 that may be, in certain embodiments, approximately twice the diameter 95 defined by the valley 75 between the prongs 92 of the tip 26'. The forcing cone 80 is formed such that the thickness 76 of the outer needle 20' is greater at the inner end 82 than at the tip 26'. In other words, the thickness at the inner end 82 is equal to the wall thickness of the tubular body of the outer needle 20' but tapers to a sharp cutting edge 78 at the tip 26'. The forcing cone 80 is formed in the inner surface 72 at an angle γ as shown in FIG. 7. In certain embodiments, the angle γ may be about 1-2° so that the countersink or forcing cone 80 forms an included angle of about 3-4°. Depending upon the wall thickness of the outer needle 20' the angle y may be as great as about 6°.

The forcing cone 80 assists in retaining the tissue within the outer needle when the device is fired and when the excised tissue is being removed. It is believed that the forcing cone tends to compress a greater volume of tissue into the outer cannula during the coring operation and that this greater volume in turn provides additional surface tension or pressure between the tissue sample and the forcing cone 80. This increased pressure allows the tissue sample to "grip" the inner surface of the outer needle as the device is being extracted from the tissue site.

The forcing cone further leads to a sharper cutting edge 78 at the tip of the outer needle. In particular, the cutting edge of an outer needle may be formed by grinding the outer surface 74 of the needle 20', either to a sharp edge or to a Franseen grind as depicted in FIG. 7 and described below. The forcing cone 80 may then be formed by grinding the inner surface 72 at an appropriate cone angle γ. The intersection between the outer and inner surface grinds thus creates a sharper cutting edge 78 than either grind alone, in part because the countersink or forcing cone 80 decreases the thickness 76 of the outer needle 20'. The thickness of the cutting edge 78 may be approximately 0.0005 to 0.001 in. in certain embodiments In another aspect, the outer needle 20' may further include a tissue slicing feature 90 formed in the outer surface 74. The tissue slicing feature 90 also reduces the thickness 76 of the outer needle 20' so that the tip 26' is the thinnest portion of the outer needle 20'. The tissue slicing feature 90 may be, for example, a Franseen tip (as described above with reference to FIGS. 5-6 and as shown in FIGS. 7-8). Other suitable slicing configurations may be a Trocar tip, a Quinke tip or any other needle point feature that forms a sharp tip and edge.

In this embodiment, the thickness 76 of the outer needle 20' varies along its length due to the introduction of the described features. The thickness 76 of the outer needle 20' between the hub 22 and the inner end 82 of the forcing cone 80 may be approximately 0.003 or 0.004 inches. The thickness 76 of the outer needle 20' begins to decrease by the angle γ at the inner end 82 of the forcing cone 80 and begins to decrease further by the angle α at the valleys 94 of the tissue slicing feature 90. The thickness 76 at the tip 26' may be thus reduced to approximately 0.0012 to 0.0014 inches.

The result of the embodiment described above, including both the countersink or forcing cone 80 and the tissue slicing feature 90, is a complete and uniform core sample trapped within the end of the outer needle 20', without any crush artifact. The tissue slicing feature 90 of the device 20' provides a cleaner cut with only linear motion and without rotation of the outer needle 20'. Furthermore, the countersink or forcing cone 80 of the device 20' provides a guiding surface to guide and support the core as it is cut away from the tissue by the cutting edge 78 of the outer needle 20'.

The angle γ and the included angle of the forcing cone or countersink 80 described above is governed, at least in part, by the tissue slicing feature 90 and the wall thickness of the outer needle 20'. As described above, in the illustrated embodiment the tissue slicing feature 90 is a Franseen tip which includes valleys or roots 94. The countersink 80 extends from the tip 26' and terminates proximal to the end of the Franseen valleys 94 at the depth D3. The depth D3 must be sufficient to draw the tissue fully into the outer needle, which in the illustrated embodiment is twice the diameter 95 of the Franseen valley. This depth, in combination with the wall thickness of the needle, determines the maximum possible angle γ. A thicker wall permits a greater angle, but at the cost of either increasing the diameter of the outer needle, which increases the diameter of the wound, or decreasing the internal diameter which decreases the diameter of the tissue sample.

In certain embodiments for obtaining a clinically suitable full core biopsy, the outer needle is formed of stainless steel tubing having a gauge of between 16 and 20. A 16 gauge needle has a nominal outer diameter of 0.0650 in.±0.0005 and an inner diameter of 0.0535 in±0.001, for a nominal wall thickness of 0.006 in. A 20 gauge needle has a nominal O.D. of 0.0350 in. ±0005 and a nominal I.D. of 0.0295 in±0.001, for a nominal wall thickness of 0.003 in. A typical Franseen grind yields a valley diameter 95 of 0.04-0.05 in., so the depth D3 in the illustrated embodiment is 0.08-0.10 in. These dimensions yield a possible angle γ in the range of 1.7-4.3° (with the shallower angle arising from a combination of the thinnest wall and the longest depth D3). However, the tip 26' of the outer needle is ground to define a cutting edge, so the larger angle γ of 4.3° can be problematic for providing as sharp a cutting edge as possible. Likewise, while a shorter depth D3 is possible, the result is a greater angle γ which may compromise the sharpness of the cutting edge. The need to maintain a sharp cutting edge also impacts the suitable angle γ that do not include the Franseen grind of the illustrated embodiment.

The outer needle 20' may include other tissue retention features formed in the inner surface 72 of the outer needle in conjunction with or in lieu of the forcing cone 80. Thus, in one feature a spiral groove 85 is formed in the inner surface 72, as shown in FIG. 8. The groove 85 may be formed in the inner surface 72 at a location adjacent the inner end 82 of the forcing cone 80. In this embodiment, the groove 85 has a depth of 0.04 to 0.08 inches. The groove 85 is shown as commencing at the end 82 of the forcing cone, although in other embodiments the groove may overlap the forcing cone. It is believed that the groove enhances the "grip" between the outer needle and the tissue being excised, particularly when combined with the forcing cone 80. It is contemplated that other tissue retention features may be incorporated into the inner surface 72 of the outer cannula. For instance, rather than a spiral groove, such as the groove 85, the feature may include a series of circumferential grooves, axial grooves, striations, ridges, knurling or other features that provide an irregular surface into which the tissue may swell. However, the spiral groove may be preferred for manufacturing reasons.

In one embodiment, the outer needle 20 of the full core biopsy device 10 may include a countersink or forcing cone 80 along with a predetermined relative positioning between the inner needle 30 and the outer needle 20'. In this embodiment, the inner needle 30 can have a length that maintains the inner needle tip 36 in a position (not shown) such that the inner needle tip 36 is situated in the outer needle 20' between the hub 22 and the inner end 82 of the countersink or forcing cone 80. In other words, the tip of the inner needle may be offset proximal or inboard of the inner end 82 of the forcing cone 80. This embodiment combines the advantages provided by the relative positioning of the inner and outer needles (in the same manner as described above in reference to the inner needle 30 and outer needle 20 of FIGS. 5-6) with the advantages provided by the forcing cone 80 as described above. Likewise, the other retention features, such as the spiral groove 85, may be incorporated into the full core biopsy device 20.

Alternatively, a tissue retention feature may incorporate a tab defined in the outer needle, such as the tab 86 defined in the outer needle 20" shown in FIGS. 9-10. The tab 86 may be defined by punching through the wall of the outer needle to form an opening 87, so that the tab is formed by part of the needle wall projecting into the inner lumen 21" of the needle. The tab 86 is sufficiently flexible or resiliently deflectable to be pushed aside by the inner needle/stylet when the device is initially charged. Once the device is fired and the outer needle projects into the tissue, the resiliently deflectable tab 86 moves past the inner needle/stylet to project inwardly and engage tissue captured within the outer needle. The tab may thus help retain the tissue within the outer needle as the device is withdrawn from the biopsy site. When the inner needle is used to eject the sample from the outer needle, the inner needle will bear against and retract the tab to release the tissue sample. In one embodiment the tab is located about 18 mm from the tip 26 of the outer needle.

The inner needle tip 36 may be closed or blocked to prevent tissue ingress into the inner needle 30. In another approach, the inner needle 30 may be integrated into an irrigation or aspiration/vacuum system. In this approach the inner needle 30 is hollow with the proximal end coupled to an irrigation or aspiration component. In order to ensure that tissue does not enter the inner needle 30, the tip 36 may be provided with a filter element that is configured to allow passage of fluids but not tissue.

Figure 11:
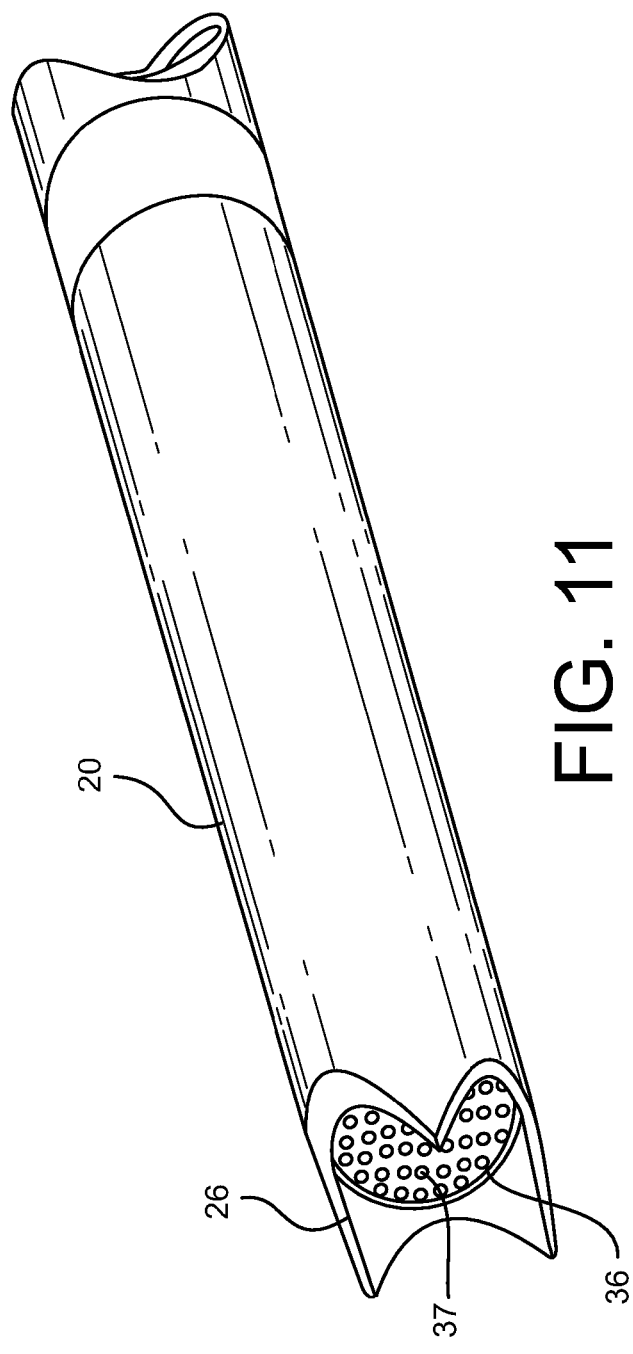
FIG. 11 is an enlarged end perspective view of an outer needle and an inner needle with a filter element for use with some embodiments of the full core biopsy core device of FIG. 1.

In one embodiment, the filter element is an etched membrane filter, such as the filter 37 shown in FIG. 11. The filter 37 may be made of 304 stainless steel and welded to the inner diameter of the hollow inner needle 30 at or adjacent the tip 36 of the needle 30. In one specific embodiment the membrane is about 0.002 inches thick with a series of 0.0037 inches diameter perforations distributed at a 0.0055 inches pitch around the area of the filter 37. Other filter element configurations are contemplated, such as a wire mesh construction.

The filter element may enhance the procedure for using the biopsy device 10 described above. For instance, in some procedures it may be desirable to apply suction at the outer needle tip 26 to help draw tissue into the outer needle 20 or to hold the tissue within the outer needle 20 as the biopsy device 10 is withdrawn from the patient. The inner needle 30 may thus be coupled to a device that provides suction at the inner needle tip 36. The filter element 37 can prevent ingress of tissue into the inner needle 30. A full core or other biopsy device can benefit from the incorporation of the filter element 37 particularly in combination with one or more of the tissue slicing feature 90, the tissue retention feature spiral groove 85, the forcing cone 80 and the relative positioning of the inner needle 30 and the outer needle 20, 20'.

Figure 13:
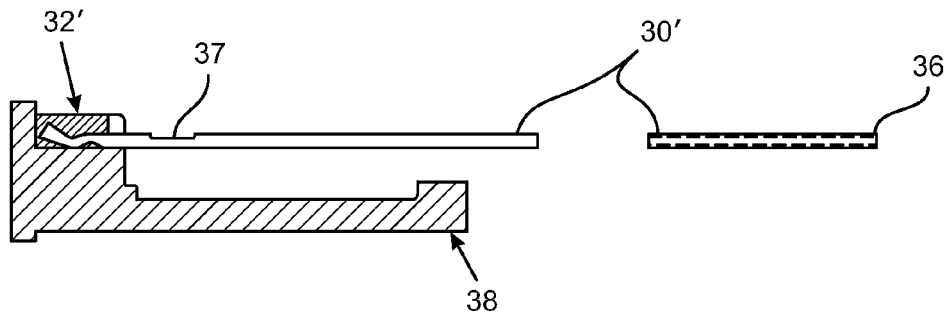
FIG. 13 is a side partial cross-sectional view of an inner needle component having a vent opening at one end for use with the full core biopsy device shown in FIG. 1.

In certain embodiments, the inner needle may be modified to provide a vent feature to relieve air pressure as the tissue sample is drawn into the outer needle 20. Thus, as shown in FIG. 13, the proximal end of an inner needle 30' is mounted in an inner needle hub 32'. The inner needle 30' further defines a vent opening 37 that communicates with the interior of the needle to the distal tip 36. The vent opening 37 eliminates any pressure head behind a tissue sample as it is drawn into the outer needle which might otherwise impede the ability of the full core biopsy device to draw a complete, intact tissue sample.

Figure 12:
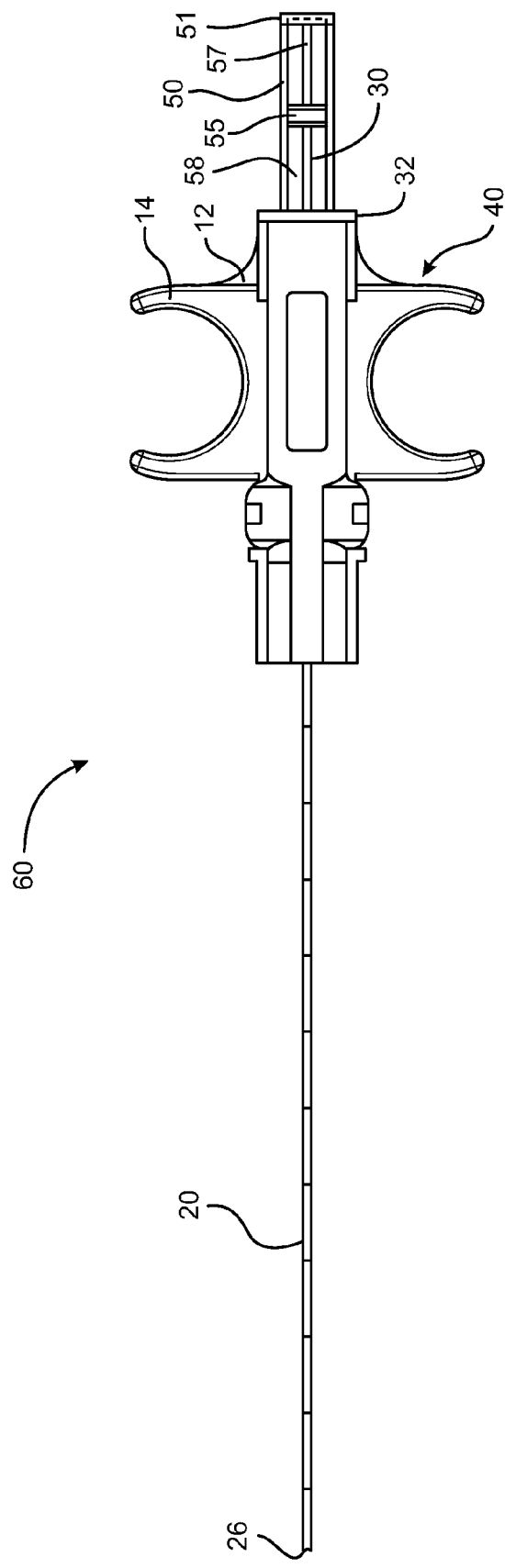
FIG. 12 is a perspective view of a full core biopsy device with a vacuum element according to one aspect of the present disclosure.

With respect to the application of suction to assist in extracting the tissue sample, it is contemplated that only a short vacuum "burst" is needed to sufficiently retain the tissue sample within the outer needle 20, 20'. Thus, while the inner needle 30 may be connected to an external vacuum source, such an approach may not be practical or necessary for many applications of the full core biopsy device 10 disclosed herein. Consequently, a biopsy device 60 shown in FIG. 12 may be modified to incorporate a vacuum generation feature. The device 60 may be similar to the device 10 described above, with substantially the same housing 12, outer needle 20 and full core tip 26, and substantially the same hub 32 supporting the inner needle 30.

In this embodiment, the biopsy device 60 is modified to incorporate a vacuum element 50 mounted in sealed engagement with the inner needle hub 32. The inner needle 30 has a length sufficient to extend from the outer needle tip 26 to (or slightly beyond) the open end 51 of the vacuum element 50. A piston 55 is mounted on the proximal end of the inner needle 30 and slidably disposed within the vacuum chamber 58. The proximal end of the inner needle 30 may be provided with a handle 57 that can be used to pull the inner needle 30 back from the tip 26 of the outer needle 20, 20'. When the handle 57 is pulled back, the piston 55 draws a vacuum within the chamber 58, which in turn pulls a vacuum within the inner needle 30. The vacuum may be enhanced if the excised tissue impinges on the distal tip 36 of the inner needle 30. The inner needle 30 may be provided with openings that communicate between the lumen of the inner needle and the vacuum chamber 58.

In some embodiments the operation of the vacuum element 50 may be coordinated and automatic with the firing of the biopsy device 60. If the vacuum element 50 is operated too soon before the tissue sample has been captured by the outer needle 20, 20' little or no vacuum will be drawn within the inner needle 30. The vacuum may thus commence when the outer needle 20, 20' approaches the end of its cutting stroke to help draw the tissue into the outer needle 20, 20'. The vacuum is preferably maintained until the outer needle 20, 20' has begun to be withdrawn from the biopsy site. In prior full core biopsy devices, when the device is being withdrawn with excised tissue, resistance in the tissue sample may tend to pull the sample back to the biopsy site and out of the biopsy device. Providing suction as the biopsy device 60 is withdrawn can resist dislodgement or retraction of the tissue sample and ensure that the sample is completely separated from the original tissue site. However, it may be preferable that the vacuum be maintained for a limited duration to avoid sucking the tissue sample into the inner needle 30 (particularly if no filter 37 is present) which may compromise the integrity of the tissue sample for subsequent histopathology. Thus, the suction may be preferably applied for a duration of less than the time to fully extract the biopsy device from the tissue site.

The amount of vacuum that can be drawn by the vacuum element 50 may be limited by limiting the stroke of the piston 55 mounted to the inner needle 30. It is contemplated that only minimal suction may be needed to ensure complete removal of the tissue sample upon withdrawal of the biopsy device 60. It is important that integrity of the tissue sample be preserved and unaffected by the suction.

In a further embodiment, the vacuum element 50 may be configured to pull the vacuum within the outer needle 20, 20'. In this case, the chamber 58 is in communication with the outer needle 20, 20', while the piston 55 remains mounted on the inner needle 30. In either embodiment, the suction is self-generated within the biopsy device 60 so no external vacuum source is necessary. This self-generation aspect insures that the amount of suction generated cannot exceed an acceptable value that might otherwise cause damage to the tissue or compromise the function of the device. Moreover, the vacuum may be generated consistently with each firing of the biopsy device 60 without the need to "reset" any components.

In some biopsy settings, it is desirable to obtain multiple tissue samples. In this case, after each firing of the biopsy device 60 the tissue sample may be dislodged by charging the outer needle 20, 20', but the position of the inner needle 30 may be unchanged (except in some cases in which the inner needle 30 is advanced slightly to assist in dislodging the tissue sample). The inner needle 30 may be biased to a starting position, not only for obtaining the sample but for generating the optimum vacuum when a sample is taken.

Figure 14:
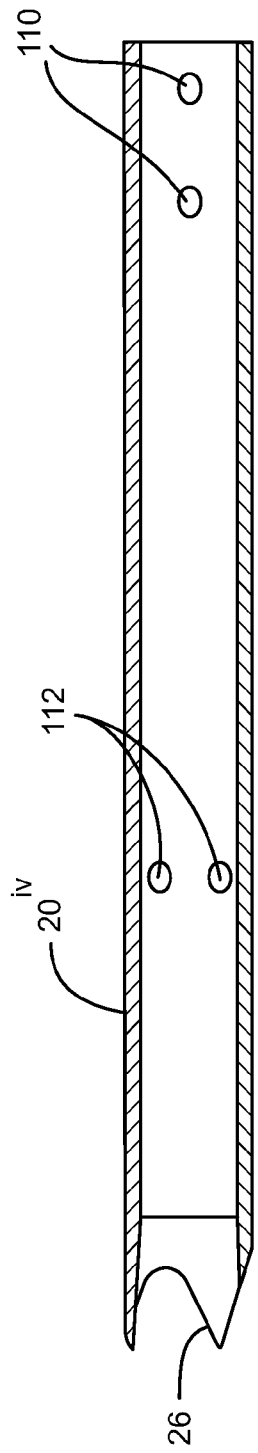
FIG. 14 is a side cross-sectional view of an outer needle component modified to include vent openings.

In the embodiment of FIG. 13, the vent feature is incorporated into the inner needle 30'. Alternatively (or additionally), a vent feature may be incorporated into the outer needle, as depicted in FIG. 14. Thus, in one embodiment, an outer needle 20$^{iv}$ may include a number of openings 110 at the proximal end of the needle. The openings may be staggered along the length of the needle, as shown, or may be disposed around the circumference of the needle. It is preferable that the openings 110 be oriented on the outer needle 20$^{iv}$ so that the openings are positioned outside the housing 12 of the device (FIG. 1) at all positions of the outer needle.

The outer needle 20$^{iv}$ may alternatively be provided with distal openings 112 adjacent the tissue receiving tip 26 of the needle. The openings may be arranged beyond the point to which a tissue sample might be expected to extend, such as about 30 mm from the tip 26. The openings may be positioned within the range of the tissue sample, i.e., within about 30 mm form the tip, in which case the tissue sample will act as a valve to close the opening(s) 112 when the sample is drawn into the outer needle. In one embodiment the openings 112 are sized to allow the tissue to extrude partially into the openings. In this embodiment the openings 112 can serve as a tissue retention feature to help hold the tissue sample within the outer cannula as it is withdrawn from the biopsy site.

Figure 15:
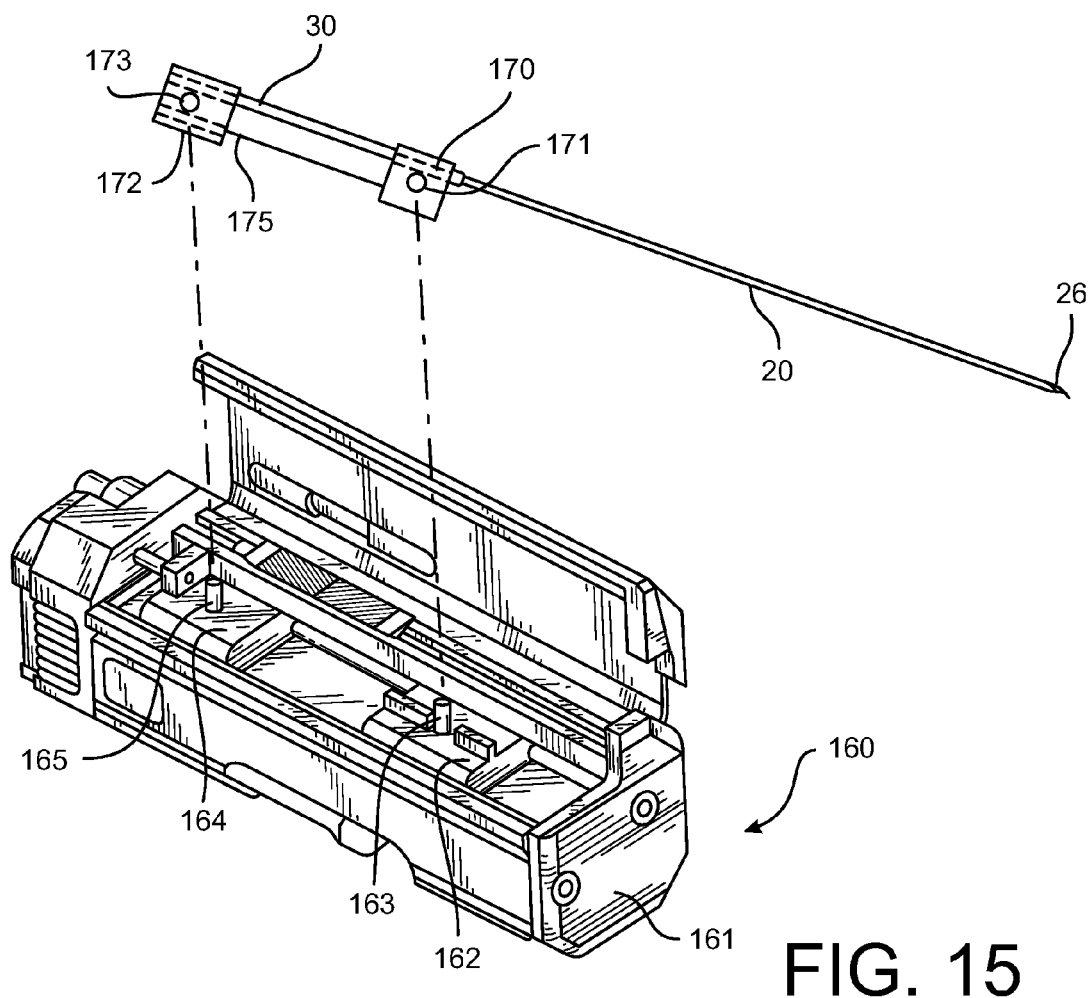
FIG. 15 is a perspective view of an automated biopsy device capable of utilizing the full core biopsy components disclosed herein.

In the embodiments shown herein, the full core biopsy components are utilized in a manual or partially automated device. The same components may be utilized in other biopsy devices. For example, the outer needle 20 (or 20') and inner needle 30 described above may be integrated into a fully automated device, such as the device 160 shown in FIG. 15. In this embodiment, the outer needle 20 is mounted to a hub 170 while the inner needle is mounted to a hub 172. The hubs are aligned by a guide pin 175 that maintains the position of the hubs for introduction into the firing device 161. The hubs 170, 172 include a respective mounting bore 171, 173 that is used to seat the hubs on a corresponding carriage 162, 164 by way of mounting pins 163, 165. Details of the construction and operation of one suitable automated device 160 are disclosed in U.S. Pat. No. 7,309,317, the disclosure of which is incorporated herein by reference. With respect to capturing a tissue sample, the device 160 operates in a manner similar to the device 10 in that the outer needle 20, 20' may be advanced into a tissue site to extract a tissue sample. The device 160 may use springs to propel the needles, as disclosed in the '317 Patent, or may implement other means for driving at least the outer needle into the tissue to be sampled.

Figure 16:
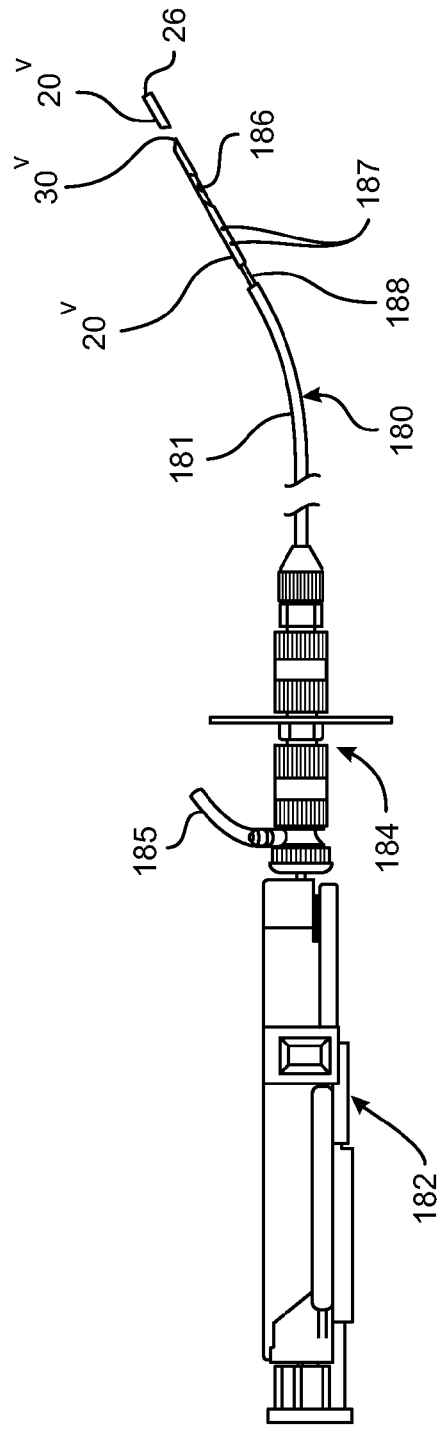
FIG. 16 is a side view of a flexible needle biopsy device capable of utilizing the full core biopsy components disclosed herein.

The full core components disclosed herein may also be used in guided, steerable or flexible biopsy devices. One such system is illustrated in FIG. 16 in which the device 180 includes a flexible needle assembly 181 mounted to a firing device 182. The device 180 may include a connector assembly 184 for incorporating an aspiration or irrigation tube 185. The device 180 and the flexible needle assembly may be constructed and operation like the biopsy device disclosed in U.S. Pat. No. 6,419,641, the disclosure of which is incorporated herein by reference. In one aspect, the flexible needle assembly includes a number of notches 186 and 188 formed in the inner needle 30$^v$ and a number of slots 187 formed in the outer needle 20$^v$. The notches and slots are arranged and aligned to allow the inner and outer needles to bend as the needle assembly is navigated through a body passage, such as through the jugular vein for transjugular access to the liver. The working end 26 of the outer needle 20$^v$ is configured as shown in FIGS. 5-6 to obtain an intact full core tissue sample. The structure and function of the inner and outer needles 20$^v$ and 30$^v$ are otherwise as described herein, with the primary difference being that the device 180 does not utilize the rigid needle approach of the devices 10, 60 and 160.

Figure 17:
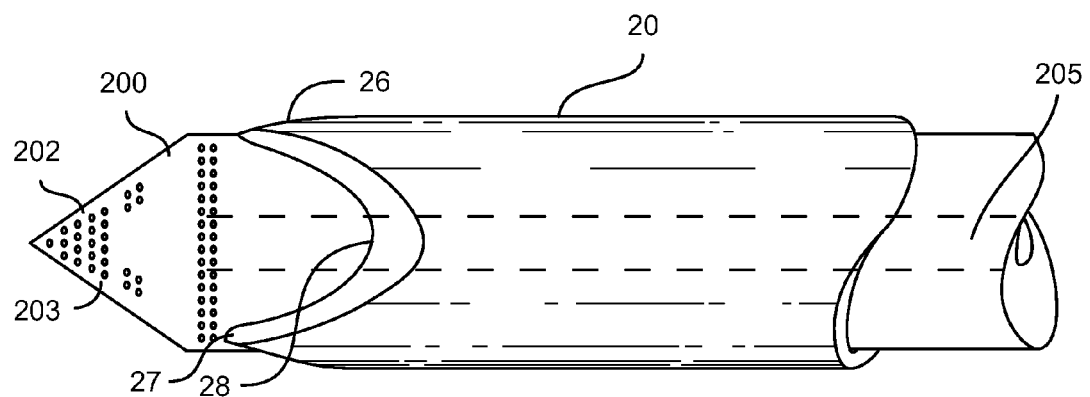
FIG. 17 is an enlarged side view of an outer needle and stylet of a full core biopsy device disclosed herein.
Figure 18:
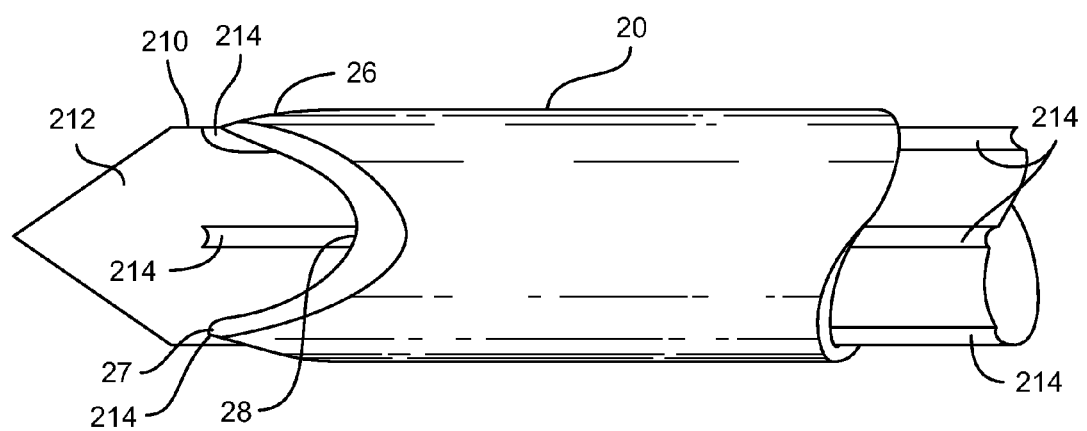
FIG. 18 is an enlarged side view of an outer needle and stylet of a further embodiment of a full core biopsy device disclosed herein.

In certain procedures it is desirable to utilize a stylet to provide initial access to the biopsy site and to act as a guide wire for advancing the outer cannula. In these procedures, the stylet must be proud of the tip of the outer cannula. Thus, as shown in FIG. 17, a stylet 200 extends beyond the prongs 27 of the outer cannula 20. The stylet 200 is configured with a sharp tip 202 configured to readily penetrate tissue. In one embodiment, the tip 202 may be formed of a porous material having a plurality of openings or interstices 203. The openings communicate with an inner lumen 205 of the stylet which may be in communication with a vent or a vacuum source, as described above. The openings 203 and lumen 205 thus provide a vent that can operate in the manner described above with respect to the filter 37 shown in FIG. 11, namely to prevent the formation of a vacuum as the stylet is retracted relative to the outer cannula 20.

In an alternative embodiment, a stylet 210 may be provided with a plurality of grooves 214 extending from the tip 212 along the length of the stylet. The grooves 214 may be in communication with a vent or a vacuum source, and function in the same manner as described above. It is contemplated that other features may be incorporated into the stylet that permit venting between the stylet and the outer cannula so that the extraction of an intact tissue sample is not compromised.

Figure 19:
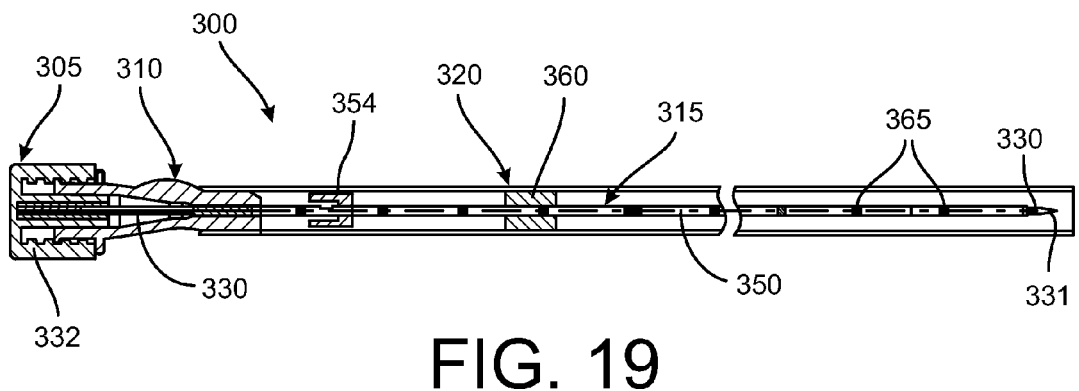
FIG. 19 is a partial cross-sectional view of an introducer assembly for use with the full core biopsy systems disclosed herein.
Figure 20:
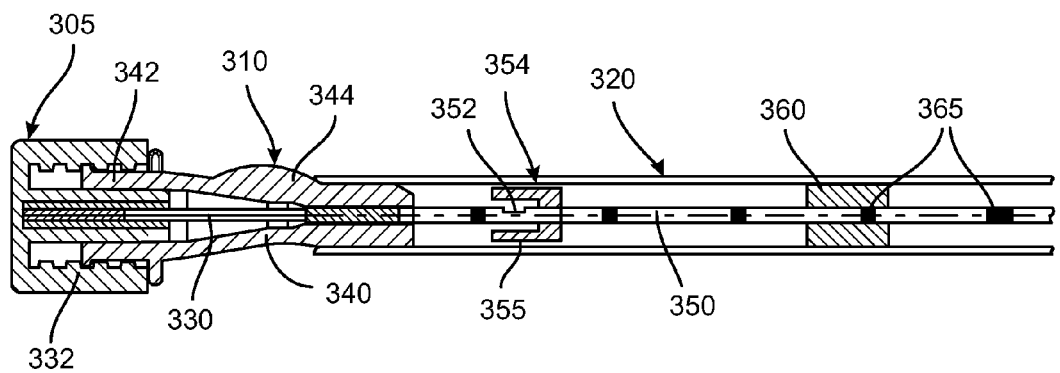
FIG. 20 is an enlarged partial view of the introducer assembly shown in FIG. 19.
Figure 21:
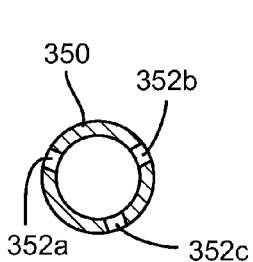
FIG. 21 is an end cross-sectional view of an alternative introducer cannula for use in the introducer assembly shown in FIG. 20.

In order to facilitate or improve the functionality of the full core biopsy devices described above, an introducer assembly 300 may be provided as illustrated in FIGS. 19-21. The introducer assembly 300 includes a stylet assembly 305, a hub assembly 310, an introducer cannula 315 mounted to the hub assembly and a protective sleeve 320. It is understood that the protective sleeve 320 is intended to conceal the sharp tip of the stylet 330 and must be removed before the introducer assembly is used.

The stylet assembly 305 includes a stylet 330 that has a tip 331 configured to pierce tissue for access to the biopsy site. The stylet and tip may have any known configuration suitable for providing biopsy access to guide the introducer cannula 315 to the site. The proximal end of the stylet may be mounted to a threaded cap 332 that is adapted to be threaded onto the fitting 342 of the hub assembly 310. The hub assembly 310 includes a body 340 that defines the fitting 342 at its proximal end. The fitting may be a Luer® fitting or other type of fitting configured for quick and simple disengagement from the stylet cap 332. The distal end 343 of the hub body 340 is configured to fix the proximal end 351 of the introducer cannula body 350 in a known manner. In one aspect, the hub body 340 may be provided with an indicator feature 310 that relates to a lateral feature on the cannula 315, as described in more detail herein. The indicator feature 315 may be a tactile indicator in the form of a tab projecting outward from the body, in the manner of the tactile indicator disclosed in U.S. Patent Re.42049, entitled "Surgical and Pharmaceutical Access Guide", which issued on Jan. 18, 2011.

The introducer cannula 315 includes an elongated hollow body 350 that is sized to receive a biopsy device, such as the full core biopsy devices described above. The hollow body is also configured to slidably receive the stylet 330 therethrough. The introducer cannula thus provides a channel to the biopsy site for introduction of the biopsy device. The cannula body 350 is sized so that the proximal end is outside the patient while the distal end of the body is at the biopsy site. Moreover, the cannula body is sized to receive a biopsy device 10 therethrough with the distal end or tip of the outer needle projecting beyond the end of the cannula. The stylet 330 is also sized so that the tip 331 of the stylet projects beyond the end of the cannula body during insertion. Preferably, the stylet projects beyond the end of the cannula body by about the same distance as the outer needle of a charged biopsy device when the device is mounted on the introducer cannula. In one embodiment, the outer needle of the charged device may project slightly further than the stylet so that the tip of the outer needle can obtain purchase in the tissue to be sampled. The introducer cannula 315 may be provided with a depth stop 360 that is slidably mounted onto the cannula body. The depth stop is adjustable along the length of the cannula body to correspond to a desired depth of insertion of the introducer assembly into the patient. The cannula body 350 may also be provided with a series of echogenic markers that can be visualized on x-ray images of the biopsy site during a procedure.

It is understood that the introducer assembly 300 is initially used to puncture and pass through tissue until the distal tip 331 of the stylet 330 is at the biopsy site. The position of the introducer assembly can be verified by imaging. When the assembly is properly positioned, the stylet assembly 305 is removed from the introducer cannula 315, leaving the cannula in place. The full core biopsy device 10 charged and is then advanced through the cannula body 350 to the biopsy site. The housing 12 of the biopsy device 10 and the hub assembly 310 may be configured so that the housing can be engaged to or mate with the hub assembly when the tip of the outer needle is at the biopsy site. In certain procedures, pressure at the biopsy site, such as hydrostatic pressure, may impede the function of the forcing cone 80 of the full core biopsy devices described herein. In other words, it is believed that certain pressures at the biopsy site can affect the ability of the forcing cone to squeeze tissue into the outer needle of the biopsy device as it is advanced into the tissue. Consequently, in one aspect of the introducer assembly 300, the cannula body 350 may be provided with a vent 352 near the proximal end 351 of the cannula body, or adjacent to the hub body 340. The vent 352 provides an avenue for excess pressure at the biopsy site to escape through the introducer cannula 315. The vent thus provides egress for fluids at the biopsy site that may generate excess hydrostatic pressure.

The introducer assembly 300 may incorporate features to prevent occlusion or blockage of the vent 352, such as by the medical personnel holding the assembly. In one feature, the indicator 344 on the hub body 340 is aligned with the circumferential position of the vent 352 so that the indicator 344 informs the medical personnel of the location of the vent. The medical personnel can then grasp the introducer assembly in a manner that will not interfere with the vent 352.

In another embodiment, a vent protector 354 may be mounted to the cannula body 350. As shown in FIG. 20, the vent protector 354 includes a shroud portion 355 that overlaps the vent 352 but is offset from the vent to form an annular space around the cannula. In one specific embodiment the vent protector 354 and shroud 355 can fully encircle the cannula 315. Alternatively, the shroud 355 can be limited to the location of the vent. The vent protector 354 is formed of a sufficiently rigid material to avoid compressing against the vent opening under manual pressure. In a further alternative, the shroud 355 may be eliminated. In this instance, the proximity of the vent protector 354 to the vent 352 will prevent the vent opening from being occluded by the medical personnel's finger or hand.

In a further embodiment, the vent may incorporate multiple openings, such as openings 352a-c depicted in FIG. 21. The openings may be dispersed around the circumference of the cannula body so that at least one opening will remain unimpeded even if the medical personnel grasps the cannula at the vent location. In the illustrated embodiment, three openings 352a-c are provided at 120° intervals; however, other orientations and numbers of openings may be provided for the vent 352.

Figure 22:
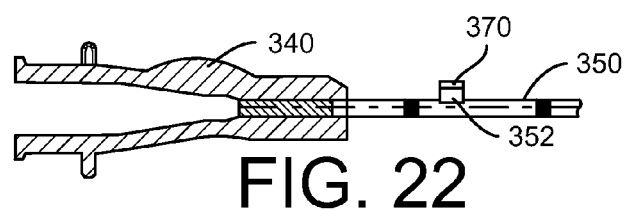
FIG. 22 is a partial view of a hub and vented introducer cannula according to a further disclosed embodiment.
Figure 23:
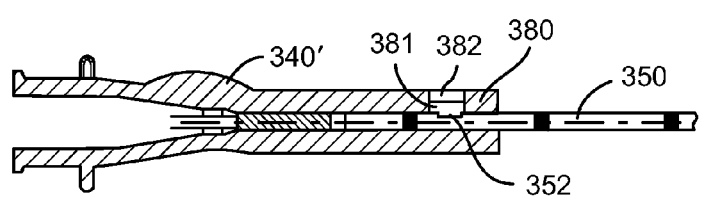
FIG. 23 is a partial view of a hub and vented introducer cannula according to yet another disclosed embodiment.

In certain instances it may be desirable to control the venting of the introducer cannula 315 in relation to the stage of advancement or operation of the introducer assembly 300 or biopsy device. In a further embodiment, the vent 352 of the introducer cannula may be provided with a valve arrangement. Thus, as shown in FIG. 22, a valve 370 may be mounted to the cannula body 350 at the vent 352. The valve may be of different configurations and may be automatic or manually operable. For instance, the valve 370 may be a poppet-type valve that releases or opens the vent 352 at a certain pressure within the introducer cannula 315. In another alternatively, the valve may be a duckbill-type valve that can be manually opened. As shown in FIG. 23, the valve may be incorporated into the hub body 340'. In this embodiment, the distal portion 380 of the hub body extends over the vent 352 and defines a vent passage 381 aligned with the cannula vent. A valve 382 may be mounted within the vent passage 381.

The introducer assembly 300 described above is particularly useful with the full core biopsy devices described herein. However, it is understood that other biopsy devices, including other full core biopsy devices, may benefit from the vented introducer cannula 315 of the present assembly 300. The vented introducer cannula may be used in conjunction with a vented biopsy device, such as the device shown in FIG. 13.

Another way to improve full core biopsy performance when using an introducer is by maintaining a certain gap between the introducer 350 and the outer needle 20 of the biopsy device 10. In particular, it has been found that performance of the biopsy device may be compromised at an introducer cannula inner diameter (I.D.) that is less than 1.2 times greater than the outer needle outer diameter (O.D.). In other words, preferred performance of the biopsy device occurs at an I.D. to O.D. ratio of 1.20 or greater, without the need for a vent in any component of the system. The I.D./O.D. ratio may be regarded in terms of gauge values, namely that the introducer cannula should have a gauge that is 2-3 steps from the gauge of the outer needle. (It is understood that the use of gauge sizes may be somewhat arbitrary in the industry and that wall thicknesses may vary). For example, in certain tests excellent performance was obtained for a 20 ga outer needle and thin-walled 17 ga introducer cannula (for a ratio of 1.53) and good results were produced by a 20 ga needle and an 18 ga introducer (a 1.20 ratio). For the two gauge step improved results may be obtained if the introducer cannula is a thin-walled cannula so that the I.D. of the cannula is larger. It has been found that devices with an O.D/I.D. ratio greater than about 1.27 provide excellent results. It has also been found that further increases in the O.D./I.D. ratio yield further improvements. An O.D./I.D. ratio of 1.45 performs about the same as if no introducer cannula was present.

Preferred performance first requires retention of the tissue sample as the device is withdrawn from the biopsy site. Another measure of performance is the length of the specimen, which is an indication of how far the tissue extended into the outer needle. Specimen length is in part a function of the "throw" of the device, or how far the outer needle is extended when the device is fired. In one embodiment, the full core biopsy device 10 can be configured for a throw of about 20.4 mm for an 18 ga outer needle. Certain devices may have a stroke as great as 33 mm or as short as 10 mm. In some instances, performance may improve as a function of the ratio between the I.D. of the needle and the throw length or stroke. For instance, for a 20 mm throw, a 19 ga needle retained a longer tissue specimen than an 18 ga needle. Thus, in certain instances improved performance can be obtained with a throw to I.D. ratio of greater than at least about 19:1. Further improved performance can be obtained with a ratio of 20:1, with ratios in the range of 23:1 to 25:1 producing very good results.

For devices with I.D./O.D. ratios less than 1.20 it is believed that the introducer may snag the tissue sample and prevent the sample from being retracted as the full core biopsy device 10 is retracted through the introducer cannula. This problem can be avoided if the introducer and biopsy device are withdrawn simultaneously. However, in most biopsy procedures this approach is not suitable. Some improvement in the performance of devices with a ratio less than 1.20 may be garnered by modifying the tip of the introducer cannula to minimize the chance that the tip will snag the biopsy sample. Thus, in one embodiment the inner surface of the introducer cannula at the tip may be siliconized to make the surface more slippery to the tissue sample. In another alternative, the introducer cannula tip is electropolished to remove any burrs and round of any sharp edges. In yet another approach a chamfer may be formed at the cannula tip.

The foregoing detailed description of one or more embodiments of the biopsy device with an inner needle disposed within an outer needle has been presented herein by way of example and not limitation. It will be recognized that there are advantages to certain individual features and functions described herein. Moreover, it will be recognized that various alternatives, modifications, variations or improvements of the above-disclosed embodiments and other features and functions, or alternatives thereof, may be desirably combined into many other different embodiments, systems or applications. Presently unforeseen or unanticipated alternatives, modifications, variations or improvements therein may be subsequently made by those skilled in the art which are also intended to be encompassed by the appended claims.

What is claimed is:

1. A biopsy assembly comprising:
 a biopsy device including;
  an outer needle hub;
  an outer needle coupled at a proximal end to the outer needle hub, the outer needle including an outer needle tip at an opposite distal end, a tissue slicing feature formed at a distalmost end of said outer needle tip and an inner lumen for receiving tissue therein extending from said distalmost end to said proximal end;
  an inner needle hub;
  an inner needle coupled at a proximal end to the inner needle hub, the inner needle including an inner needle tip at an opposite distal end, the inner needle being coaxially disposed within the lumen of said outer needle; and
  a mechanism coupled to said outer needle hub and said inner needle hub for charging and firing said outer needle relative to said inner needle to capture a tissue sample within the lumen of said outer needle, an introducer cannula having a length less than the length of said outer needle and defining a lumen sized to receive the outer needle of said biopsy device, said lumen open at a proximal end to receive said biopsy device therein and open at a distal end for extension of said outer needle upon firing said outer needle by said mechanism, wherein said introducer cannula defines a number of openings adjacent said proximal end for venting pressure within said introducer cannula upon firing said outer needle by said mechanism; and a vent protector disposed on said introducer cannula adjacent at least one of said number of openings, said vent protector configured to prevent occlusion of said at least one opening by a person manipulating the cannula.

2. The biopsy assembly of claim 1 wherein said outer needle has an outer diameter and said lumen of said introducer cannula has an inner diameter that is at least 1.20 times greater than said outer diameter.

3. The biopsy assembly of claim 2, wherein said inner diameter of said introducer cannula is about 1.27 times greater than said outer diameter.

4. The biopsy assembly of claim 3, wherein said inner diameter of said introducer cannula is less than about 1.45 times greater than said outer diameter.

5. The biopsy assembly of claim 2, wherein said inner lumen of said outer needle includes a countersink defined at said outer needle tip.

6. The biopsy assembly of claim 5, wherein the countersink is tapered from said distalmost end of said outer needle.

7. The biopsy assembly of claim 6, wherein said countersink is tapered at approximately a one to two degree angle relative to the inner surface.

8. The biopsy assembly of claim 1, wherein said inner lumen of said outer needle includes a countersink defined at said outer needle tip.

9. The biopsy assembly of claim 8, wherein the countersink is tapered from said distalmost end of said outer needle.

10. The biopsy assembly of claim 9, wherein said countersink is tapered at approximately a one to two degree angle relative to the inner surface.

11. The biopsy assembly of claim 1, wherein said vent protector includes a shroud overlapping but offset from said at least one opening.

12. The biopsy assembly of claim 1, further comprising a valve associated with at least one of said number of openings, said valve configured to controllably open or close said at least one opening.

13. The biopsy assembly of claim 12, wherein said valve is configured to open at a predetermined pressure within the introducer cannula.

14. The biopsy assembly of claim 13, wherein said valve is manually operable.

* * * * *